(12) United States Patent
Shiozawa

(10) Patent No.: US 7,615,538 B2
(45) Date of Patent: Nov. 10, 2009

(54) METHOD FOR THERAPY OF RHEUMATOID ARTHRITIS

(76) Inventor: Shunichi Shiozawa, 11-6, Takenodai 2-chome, Nishi-ku, Kobe-shi, Hyogo 651-22 (JP)

( * ) Notice: Subject to any disclaimer, the term of this patent is extended or adjusted under 35 U.S.C. 154(b) by 438 days.

(21) Appl. No.: 10/440,256

(22) Filed: May 19, 2003

(65) Prior Publication Data
US 2004/0006038 A1    Jan. 8, 2004

Related U.S. Application Data

(63) Continuation of application No. 09/514,339, filed on Feb. 28, 2000, now abandoned, which is a continuation-in-part of application No. 08/637,676, filed as application No. PCT/JP93/01581 on Oct. 29, 1993, now abandoned.

(51) Int. Cl.
A61K 48/00    (2006.01)
C07H 21/04    (2006.01)

(52) U.S. Cl. .................. 514/44; 536/23.1; 536/24.5; 536/24.31; 536/24.33

(58) Field of Classification Search .............. None
See application file for complete search history.

(56) References Cited

U.S. PATENT DOCUMENTS

2005/0113400 A1 *    5/2005    Chaki et al. .................. 514/277

FOREIGN PATENT DOCUMENTS

| EP | 0 733 370 A1 * | 9/1996 | .............. 514/44 |
|----|----|----|----|
| WO | WO91/06570 | 5/1991 | |
| WO | 91/11535 | 8/1991 | |
| WO | 92/07072 | 4/1992 | |
| WO | WO92/07072 | 4/1992 | |
| WO | 92/18522 | 10/1992 | |
| WO | 93/14768 | 8/1993 | |

OTHER PUBLICATIONS

Scherer et al., Approaches for the sequence-specific knockdown of mRNA, 2003, Nat. Biotechnol., 21(12), pp. 1457-1465.*
Mahato et al., Modulation of gene expression by antisense and antigene oligodeoxynucleotides and small interfering RNA, Jan. 2005, Expert Opinion on Drug Delivery, vol. 2, No. 1, pp. 3-28.*
Cho-Chung et al., CRE-decoy oligonucleotide-inhibition of gene expression and tumor growth, 2000, Molecular and Cellular Biochemistry, 212, pp. 29-34.*
Yoshida et al., Nucleic Acids Research 21(11):2715-2721 (1993).
Shiozawa et al., J. virol. 148(10):3100-3104 (1992).
Richardson et al., Drugs 50(Suppl. 1):26-36(1995).
Harris, Current Opinion in Rheumatology 6:287-289(1994).
Wilder et al., Clinical Orthopaedics and Related Research 265:36-41(1991).

J. Alam et al., "Distal AP-1 Binding Sites Mediate Basal Level Enhancement and TPA Induction of the Mouse Heme Oxygenase-1 Gene", The Journal of Biological Chemistry, vol. 267, No. 30, pp. 21894-21900 (1992).
Müller-Ladner et al., Scand. J. Rheumatol. 24 (Suppl 101): 115-119 (1995).
Van Lent et al., Scand. J. Rheumatol. 24 (Suppl 101):83-89 (1995).
Zvaifler, Scand. J. Rheumatol. 24 (Suppl 101):67-75 (1995).
Bielinska, A. et al: "Regulation of gene expression with double-stranded phosphorothioate oligonucleotides" Science, vol. 250, 1990, pp. 997-1000.
Ritchlin, C. T. et al: "Potential mechanisms for coordinate gene activation in the rheumatoid synoviocyte: Implications and hypotheses" Springer Seminars in Immunopathology, vol. 11, 1989, pp. 219-234.
Shiozawa, S. et al: "Contribution of synovial mesenchymal cells to the pathogenesis of rheumatoid arthritis" Seminars in Arthritis and Rheumatism, vol. 21, No. 4, 1992, pp. 267-273.
Kuroki, Y. et al: "The contribution of human c-fos DNA to cultured synovia cells: a transfection study" The Journal of Rheumatology, vol. 20, No. 3, Mar. 1993, pp. 422-428.
Shiozawa, S. et al: "Destructive arthritis without lymphocytic infiltration in H2-c-fos transgenic mice" The Journal of Immunology, vol. 148, No. 10, May 15, 1992, pp. 3100-3104.
Kuroki, Y et al: "Constitutive expression of c-fos gene inhibits type 1 collagen synthesis in transected osteoblasts" Biochemical and Biophysical Research Communications, vol. 182, No. 3, 1992, pp. 1389-1394.
Holt, J.T. et al: "Inducible production of c-fos antisense RNA inhibits 3T3 cell proliferation" Proceedings of the National Academy of Sciences USA, vol. 83, 1986, pp. 4797-4798.
Takahashi, H. et al: "Anaylsis of the 5' -upstream promoter region of human involucrin gene: activation by 12-0-tetradecanoylphorbol-13-acetate" The Journal of Investigative Dermatology, vol. 100, No. 1, Jan. 1993, pp. 10-15.
Angel, P. et al: "Phorbol ester-inducible genes contain a common cis element recognized by a TPA-modulated trans-acting factor" Cell, vol. 49, 1987, pp. 729-739.
Anfossi, G. et al: "An oligomer complementary to c-myb-encoded mRNA inhibits proliferation of human myeloid leukemia cell lines" Proceedings of the National Academy of Sciences, USA, vol. 86, May 1989, pp. 3379-3383.

* cited by examiner

*Primary Examiner*—Amy Bowman
(74) *Attorney, Agent, or Firm*—Wenderoth, Lind & Ponack, L.L.P.

(57) ABSTRACT

The invention provides a method for therapy of rheumatoid arthritis, which comprises administering double-stranded oligonucleotide comprising the nucleotide sequence of 5'-TGAGTCA-3' to a patient who suffers rheumatoid arthritis.

1 Claim, No Drawings

METHOD FOR THERAPY OF RHEUMATOID ARTHRITIS

This application is a continuation application of Ser. No. 09/514,339 filed Feb. 28, 2000 now abandoned, which is a continuation-in-part application of Ser. No. 08/637,676 filed Jul. 11, 1996 now abandoned, which is a U.S. national stage of International Application No. PCT/JP93/01581 filed Oct. 29, 1993.

BACKGROUND OF THE INVENTION

1. Field of the Invention

The present invention relates to a method for therapy of rheumatoid arthritis. In particular, the present invention relates to a therapeutic method for rheumatoid arthritis by using a AP-1 oligonucleotide for inhibiting the intracellular signal of the c-fos gene expression product.

2. Description of the Related Art

Chronic rheumatoid arthritis (RA) is still one of many intractable diseases of which the cause is not as yet known, though the morbidity rate is as high as 0.3% of the population.

The process in RA is considered to be divided into the following 3 stages, and practically there are evidences that those processes are ongoing in the articular synovial membrane of RA (E. D. Harris, Jr., *N. Engl. J. Med.*, 322: 1277-1289, 1990; S. Shiozawa and K. Shiozawa, *Scand. J. Rheumatol. Suppl.*, 74:65-72, 1988). At the 1st stage, an unknown pathogenic factor reaches the articular synovial membrane from blood to initiate immune response at the articular region. At the 2nd stage, macro-phages, lymphocytes, neutrophils and so on infiltrate from blood to develop chronic inflammation. At the 3rd stage, i) cartilage matrix is degradated and digested by protease released from the inflamed synovial membrane; ii) cartilage and bone are destroyed by pannus derived from inflammatory granulation tissue; and iii) cartilage cells per se are activated to degradate peripheral matrix, and so on; such multiple progresses result in destruction and deformation of the joint.

In such an articular lesion of RA, two species of cells, i.e., T cells which are responsible for immunological memory to response specifically to antigens, and mesenchymal cells in synovial membrane which participate directly in the articular destruction, are considered to be basically important. Among them, it has been found that the latter mesenchymal cells are major components for pannus and produce cytokines such as interleukin (IL)-1, IL-6, tumor necrosis factor (TNF), etc., which play an important role in joint inflammation of RA, to actively participate in destruction of the joint (S. Shiozawa, et al., *Arthritis Rheum.*, 26:472-478, 1983). Thus, the RA is considered to be caused first by antigen-specific response involving T cells. It is further considered that at the stage at which the inflammation becomes lentus to result in a chronic condition, growth factors, cytokines, etc. are produced in large quantities to strongly activate the synovial cells of the articular region, particularly mesenchymal cells.

It is considered that when the synovial membrane is activated, then the cell-mediated articular destruction progresses automatically to some extent. On the other hand, a protooncogene c-fos, among genes involved in cell growth, is characterized by being continuously expressed in mesenchymal cells, particularly such as macrophages or synovial cells, without any stimulation. Pannus being composed of synovial cells is semi-tumor-like granulation tissue which may be described as "transforming". In practice, when experimental arthritis was induced in H2-c-fos transgenic mice overexpressing human c-fos gene, the articular destruction was produced only by the mesenchymal cells of synovial membrane without infiltration of lymphocytes (T cells) (S. Shiozawa and T. Tokuhisa, *Sem. Arthritis Rheum.*, 21:267-273, 1992). This means that over expression of the c-fos gene by gene manipulation gave the nearly autonomic proliferation potency to the mesenchymal cells of synovial membrane, and it was demonstrated that the activated synovial cells invaded as pannus into cartilage matrix (S. Shiozawa, et al., *J. Immunol.*, 148: 3100-3104, 1992). Moreover, it was found that the c-fos gene afforded peculiar morphological transformation and proliferation potency to human synovial cells, that when the human c-fos gene was continuously expressed in osteoblasts, the synthesis of bone matrix collagen was inhibited (Y. Kuroki, et al., *J. Rheumatol.*, 20:422-428 (1993), and that osteoclastic bone resorption mediated by osteoblasts was significantly promoted (Y. Kuroki, et al., *Biochem. Biophys. Res. Commun.*, 182:1389-1394, 1992). In other words, it was found that the basic and major pathological condition of RA, i.e., "proliferation of synovial cells" and "osteoporosis" in periarticular bone, could be reproduced experimentally by means of merely promoting the expression of c-fos gene.

SUMMARY OF THE INVENTION

From the evidences set forth in the Related Art, the present inventor concluded that an artificial inhibition of intracellular signaling of the c-fos gene product must lead to an important therapy of RA. Furthermore, the present inventor found out that the c-fos gene product acts as an transcription factor binding to the "AP-1" sites of RA relating genes, and an oligonucleotide antagonizing such binding can be used as a means for inhibiting the signal of c-fos product (hereinafter referred to as "c-fos/AP-1").

The present invention has been made in accordance with the above findings by the inventor, and the present application provides a method for therapy of rheumatoid arthritis, which comprises administering a double-stranded oligonucleotide comprising the nucleotide sequence of 5'-tgagtca-3' to a patient who suffers from rheumatoid arthritis.

In the method of the present invention, it is an embodiment that the double-stranded oligonucleotide consists of the nucleotide sequences of SEQ ID No. 1 and SEQ ID No. 2.

DESCRIPTION OF THE PREFERRED EMBODIMENTS

The method of the present invention based on the pathogenic and pathological process of RA is as follows:

(i) Over expression of c-fos
(ii) Activation of c-fos/AP-1 signal
(iii) Expression of various genes
(iv) Proliferation of mesenchymal cells (synovial cells)
(v) Articular destruction by pannus
(vi) Occurrence of RA The method of the present invention aims to disrupt the progress from phase (ii) to (iii) by administering a double-stranded oligonucleotide comprising the nucleotide sequence of 5'-tgagtca-3'.

The promoter region of RA relating genes contains the following nucleotide sequence:

```
5'-gtgttaccctgagtcagaggagaa-3'    (SEQ ID No: 1)

3'-aatgggactcagtctcctcttggg-5'    (SEQ ID No: 2)
``` and the underlined sequence is the AP-1 binding site to which c-fos/AP-1 binds. The double-stranded oligonucleotide of this invention (hereinafter referred to as "AP-1 oligonucleotide") hybridize with the AP-1 site and prevents the c-fos/AP-1 to bind the AP-1 site.

The inhibition of gene expression by using the AP-1 oligonucleotide is triggered by "antisense therapy" (P. O. P. Ts'o et al., *Ann. NY. Acad. Sci.*, 507:220-241, 1987). The principle of the antisense therapy was proposed in the mid-1970's (P. S. Miller, et al., *Biochemistry*, 16:1988-1996, 1977), and now has been investigated as one of most probable gene therapies. The use of AP-1 oligonucleotide would also be probable for the therapy of RA, but the principle is basically different from antisense technology. That is, in a human cell, a mRNA encoding a double-stranded DNA is transcribed from one-side of the DNA strand (sense strand or template strand), and then a protein is translated from the mRNA. In antisense inhibition, the mRNA is hybridized with the antisense RNA (single strand) having a sequence complimentary to the mRNA, to thereby arrest the translation of the mRNA. On the other hand, the present invention intends to control the gene expression by hybridizing the double-stranded AP-1 oligonucleotide directly with the gene promoter AP-1 site to which the transcription factor c-fos/AP-1 binds.

The double-stranded AP-1 oligonucleotide is prepared, for example, by annealing an oligonucleotide having the sequence of 5'-tgagtca-3' with another oligonucleotide having the sequence of 5'-tgactca-3' in a solution. The length of the oligonucleotide might be arbitrary arranged from 12 to 30bp.

The double-stranded AP-1 oligonucleotide can be administered in a form of capsule or injection drug. Such pharmaceutical preparations can be formed together with a pharmaceutically acceptable carrier, vehicle etc., and be given to the patient through oral or non-oral administration. In the case of injection drugs, the double-stranded AP-1 oligonucleotide can be dissolved or emulsified with an aqueous or fatty solution usually used for preparation of injection drugs, and can be administrated by means of subcutaneous, intra-dermal, intra-muscular or intra-articular injection. The AP-1 oligonucleotide would be capsulated with liposome, or mixed with cationic lipid. The dose amount of the AP-1 oligonucleotide is variable according to age, body weight and symptoms of the patient, and it is preferable for the adult patient to be addministered 10 μg to 10 mg per day. The double-stranded AP-1 oligonucleotide would be administered at the time when any symptom of arthritis is detected. Alternatively, for high risk persons who have a genetic background for rheumatoid arthritis, it is recommended to administer the oligonucleotide when they are middle aged.

As mentioned above, since c-fos is a gene for the growth of not only articular synovial cells but also macrophages and other mesenchymal cells, the inhibition of c-fos/AP-1 signal is considered to inhibit the proliferation of a variety of mesenchymal cells. As for diseases in which the proliferation of mesenchymal cells are involved, for example, hypertrophy (proliferation of foam macrophages, fibroblasts, smooth muscle cells, etc.) of the intima observed in atherosclerosis, mesangial glomerules nephritis (proliferation of mesangial cells), liver cirrhosis (proliferation of fibroblasts), and so on are exemplified. Accordingly, it is expected that AP-1 oligonucleotide of this invention would be effective against these diseases.

EXAMPLES

The present invention will now be described further in detail by means of Examples.

Example 1

A pharmaceutical preparation containing the AP-1 oligonucleotide was prepared as follows.

In 40 mM Tris-HCl buffer (pH 7.5) containing 20 mM $MgCl_2$ and 50 mM NaCl, the oligonucletides consisting of the sequence of SEQ ID Nos. 1 and 2 were dissolved in the amount of 35 mg each, and the total volume was made 72 ml in a polycarbonate vessel. This solution was kept at 70° C. in a hot bath for 5 minutes and then held until the water temperature decreased 30° C. for annealing. The solution was filtered through a filter of 0.22 μmpore size under a sterilized condition. The filtrate was immediately diluted 10 times with physiological saline for injection, and filled into sterilized vials to give 1 ml vial preparations for injection. The resulting preparations contained 102 μg/1 ml/vial of the double-strand AP-1 oligonucleotide:

5'-gtgttaccc<u>tgagtca</u>gaggagaa-3'    (SEQ ID No:1 )

3'-aatggg<u>actcagt</u>ctcctcttggg-5'    (SEQ ID No: 2)

and pH value of this preparation was 7.7.

Moreover, all of the results of a sterility test, a foreign insoluble test, a pyrogen test and a local irritation test were acceptable.

Example 2

The therapeutic effect of AP-1 oligonucleotide was tested with a RA animal model.

DBA/1J male mice were subcutaneously immunized with FCA and 200 μg of type II collagen twice at a time interval of three weeks, and after two weeks from the initial immunization, and the pharmaceutical preparation of EXAMPLE 1 was intraperioneally injected at twice per week. In this procedure, 5 μg of AP-1 oligonucleotide was administered in each injection. A nonspecific double-stranded oligonucleotide of 24 bp was used for a control. Upon three weeks from the second immunization, the foot joints were subjected to histological examination.

As a result, the hyperplasta of foot pad (>3.7 mm) was observed in 6/14 mice (43%) for the drug-treated group and 12/16 (75%) for the control group. A histologically remarkable inflammatory cell infiltration was observed in 7/14 animals (50%) for the drug-treated group, and 8/16 (50%) for the control group. No differences were observed in increasing rate of body weight of mice before and after experiment: 151% for the treated group and 144% for the control group.

On the other hand, the cases showing no damage in joints were 12/14 animals (86%) for the treated group, and 2/16 animals (13%) for the control group.

Furthermore, on in vitro observation of synovial cell culture derived from the drug-treated mice, it was confirmed that the AP-1 oligonucleotide inhibited the expressions of IL-1 and the like which are activated through the AP-1 site, but had no effect on gene expressions not through the AP-1 site.

As is clear from the in vivo results, the double-stranded AP-1 oligonucleotide significantly reduced the joint destruction of collagen-induced arthritis in mice. However, there was no difference in the extent of inflammatory cell infiltration to local lesions of joints between two groups. These results suggest that, in arthritis, the filtration of inflammatory cell do not necessarily directly participate in joint destruction, which agrees with the result in H2-c-fos transgenic mice in which the articular destruction was produced only by the mesenchymal cells of synovial membrane without infiltration of T cells (S. Shiozawa and T. Tokuhisa, *Sem. Arthritis Rheum.*, 21:267-273, 1992).

Furthermore, it should be noted that mouse collagen arthritis is accepted as an excellent model for investigating the immunological phenomenon which is responsible for the progression of arthritis occurring in human RA. For example, it has been found that non-steroidal anti-inflammatory drugs (NSAIDs) supposed to be poor in effectiveness to human RA have almost no activity to this arthritis model (K. Phadke, et al., *Immun. Pharmacol.*, 10:51-60, 1985). On the other hand, since the progress of the arthritis was apparently prevented by steroidal drugs and immunosuppressors, it has been demonstrated that this model might be useful in finding out new types of anti-rheumatic agents. Moreover, this model has been confirmed to be useful in all of drugs including methotrexate (MTX) which is supposed to be most effective in drug therapy of human RA as well as drugs under clinical trial. Accordingly, the mouse collagen arthritis used in this Example 1 is considered to be utilizable in estimating the therapeutic efficacy at least to RA.

Example 3

A program for administration trials of the AP-1 oligonucleotide for RA patients was carried out with the approval of the Ethical Committee of the School of Medicine, Kobe University, Hyogo JAPAN.

In carrying out this clinical administration trial, the following two RA patients who understood the clinical significance of this trial and consented to voluntarily become subjects for the trial were employed. In order to carefully examine adverse reaction, the drug preparation of Example 1 which contains the double-stranded AP-1 oligonucleotide was injected intra-articularly to unilateral knee joint first at a dose of 2 μg a week, and the dosage was then increased every week to 5 μg, 20 μg and 50 μg, so that the injection was complete 4 times. The observation was continued for a period of 2 weeks after termination of the injection to observe the clinical condition, articular findings and the results of clinical tests. The followings indicate the background of the patients and typical examples of the change in clinical findings. No adverse reaction from the administration of the preparation was observed in any patients.

Patient 1: 73 years of age, male, body weight 41 kg, hospitalized
RA diagnosis: Classical, Stage I, Class 2,
Disease duration: 9 months
Complication: none
Anamnesis: duodenal ulcer
Allergic anamnesis: none Patient 2: 66 years of age, female, body weight 32.9 kg, hospitalized
RA diagnosis: Classical, Stage III, Class 2,
Disease duration: 3 years and 5 months
Complication: none
Anamnesis: pulmonary tuberculosis
Allergic anamnesis: none The results of the test are shown on Tables 1 and 2. From the results, it is noteworthy in the effect of the present drug that both the swollen joint count and CRP decreased in both patients. Additionally, adverse reaction and abnormal values in laboratory tests could not be recognized, and the impression of the patients was also appreciated; this means that the present pharmaceutical preparations are very useful as a therapeutic means for RA.

TABLE 1

| Test Item | Patient 1 | Patient 2 |
| --- | --- | --- |
| Findings of articular region: | | |
| Administered side: | No change | Improved |
| Non-administered side: | No change | No change |
| Patient's assessment of pain: | No change | Improved |
| Physician's global assessment: | No change | Improved |

TABLE 2

| | | Patient 1 | | Patient 2 | |
| --- | --- | --- | --- | --- | --- |
| Test Item | | Before | After | Before | After |
| Tender joint count: | | 1 | 2 | 5 | 6 |
| Swollen joint count: | | 25 | 18 | 11 | 5 |
| Morning stiffness (min.): | | 0 | 0 | 30 | 0 |
| Grip strength (mmHg) | Right: | 64 | 98 | 78 | 85 |
| | Left: | 52 | 94 | 72 | 80 |
| CRP (mg/dl): | | 9.5 | 4.4 | 9.6 | 7.7 |
| ESR (mm): | | 96 | 94 | 126 | 106 |

Note:
the values underlined indicate improvement.

As is clear from the above clinical trials, the double-stranded AP-1 oligonucleotide should be effective for therapy of human RA, and would be effective for prevention of RA.

What is claimed is:

1. A method of treating rheumatoid arthritis, the method comprising administering a double-stranded oligonucleotide to a patient who suffers from rheumatoid arthritis to inhibit joint destruction in said patient, wherein the double-stranded oligonucleotide consists of the nucleotide sequences of SEQ ID NOs: 1 and 2.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Artificial sequence
<220> FEATURE:
<223> OTHER INFORMATION: Description of Artificial Sequence: SYNTHETIC NUCLEIC ACID -continued

```
<400> SEQUENCE: 1
gtgttaccct gagtcagagg agaa    24

<210> SEQ ID NO 2
<211> LENGTH: 24
<212> TYPE: DNA
<213> ORGANISM: Artificial sequence
<220> FEATURE:
<223> OTHER INFORMATION: Description of Artificial Sequence: SYNTHETIC
      NUCLEIC ACID

<400> SEQUENCE: 2
gggttctcct ctgactcagg gtaa    24
```